US00PP11958P2

(12) United States Plant Patent
Catt

(10) Patent No.: US PP11,958 P2
(45) Date of Patent: Jun. 26, 2001

(54) CARYOPTERIS PLANT NAMED 'FIRST CHOICE'

(76) Inventor: Peter Catt, Liss Forest Nursery, Petersfield Road, Greatham, Liss, Hampshire GU33 6HA (GB)

( * ) Notice: Subject to any disclaimer, the term of this patent is extended or adjusted under 35 U.S.C. 154(b) by 0 days.

(21) Appl. No.: 09/262,990

(22) Filed: Mar. 5, 1999

(51) Int. Cl.[7] ..... A01H 5/00
(52) U.S. Cl. ..... Plt./226
(58) Field of Search ..... Plt./226

(56) References Cited

PUBLICATIONS

Huxley, A., Griffiths, M., Levy, M.. The New Royal Horticultural Society Dictionary of Gardening. vol. 2, Jul. 10, 1992.*

* cited by examiner

*Primary Examiner*—Bruce R. Campell
*Assistant Examiner*—Michelle Kizilkaya
(74) *Attorney, Agent, or Firm*—Mark P. Bourgeois

(57) ABSTRACT

A new variety of Bluebeard plant named 'First Choice', characterized by abundant deep blue-violet flowers that bloom over a long period, deep green foliage and a compact growth habit.

2 Drawing Sheets

BACKGROUND OF THE INVENTION

This invention presents a new and distinct cultivar *Caryopteris×clandonensis* and will be referred to hereafter by the cultivar name 'First Choice'. 'First Choice' is a new an distinct cultivar of Bluebeard, a shrub that is grown as a perennial for landscape use.

The new cultivar is the result of a seedling selection program that began in 1988 with the objective of developing a cultivar with a compact plant habit and a stronger flower color. Seeds were originally collected by the inventor at Liss Forest Nursury in Hampshire, UK. Seedlings were selected, open-pollinated, and reselected over five subsequent generations. Seeds were originally collected from the cultivars *Caryopteris×clandonensis* 'Heavenly Blue' (unpatented) and *Caryopteris×clandonensis* 'Kew Blue' (unpatented). In five subsequent generations, the most promising seedlings were selected, open-pollinated and observed for further seed collection. The new Caryopteris was discovered in a seed bed sown of these various unidentified crosses of *Caryopteris×clandonensis* seed in 1992. Thousands of seedlings were evaluated before the cultivar 'First Choice' was selected as unique in that it has a compact growth habit, a long bloom season and deep-colored floral buds and flowers. The new cultivar is more similar to 'Kew Blue' than to 'Heavenly Blue'. 'First Choice' differs from 'Kew Blue' in that 'First Choice' is longer blooming, more compact, the flowers are larger and richer in color, the flowers are more abundant, and the foliage is greener. Data is given Table 1 for comparison to 'Dark Knight' (unpatented) because the flower color of 'Dark Knight' is closer to that of 'First Choice' than any other cultivar. The new cultivar can be readily distinguished from all other cultivars of *Caryopteris×clandonensis* by the characteristics that are described hereafter.

Asexual propagation of the new cultivar has been accomplished by semi-ripe cuttings taken by the inventor in 1994 at Liss Forest Nursery in England. The characteristics of this new cultivar have been determined to be stable and are reproduced true to type in successive generations.

SUMMARY OF THE INVENTION

The following traits have been repeatedly observed and are determined to be characteristics of the new cultivar. The combination of these traits distinguish the new cultivar from all others in commerce.

1. 'First Choice' has a long bloom season. A high proportion of early flower buds on 'First Choice' develop into flowers, whereas the early season flower buds of other known cultivars often do not fully develop.

2. The flowers of 'First Choice' are borne in profusion on erect stems.

3. The floral buds are inky-blue in color and the flowers are a deep lilac-blue.

4. The plant habit is compact.

5. The foliage is a deep green with a satin finish; other cultivars are typically grey-green.

BRIEF DESCRIPTION OF THE DRAWING

On sheet one, the entire plant is shown to depict the plant habit of 'First Choice'. Sheet two depicts an individual bloom that is as close as reasonably possible by conventional photography and a photo showing the cultivar 'Longwood Blue' (left) next to the cultivar 'First Choice' to demonstrate the difference in plant habit and flower color.

BOTANICAL DESCRIPTION OF THE PLANT

The following is a detailed description of the new cultivar as on 2 year old plants grown outdoors in Monkton, Md. in 3-gallon containers. Phenotypic differences may be observed with variations in environmental, climatic, and cultural conditions. The color determination is in accordance with The R.H.S. Colour Chart of The Royal Horticultural Society, London, England, except where general color terms of ordinary dictionary significance are used.

Botanical classification: 'First Choice' is a cultivar of *Caryopteris×clandonensis.*

Parentage:

*Seed parent.*—Unidentified *Caryopteris×clandonensis* seedling selection.

*Pollen parent.*—Unidentified *Caryopteris×clandonensis* seedling selection.

Commercial classification: Bluebeard.

Garden use: A sub-shrub that is treated as a perennial landscape plant.

Plant description:

*Blooming period.*—Early August to late September.

*Blooming habit.*—Axillary and terminal blooms, produced on new wood.

*Disease resistance.*—No known disease or insect problems.

*Culture.*—Prefers full sun, well-drained soil. Drought tolerant.

*Fruit.*—Dry, 4-valved capsule separated into a 4 winged nutlet, 4 mm in length, 3 mm in width, color 143A when immature gradually changing to a purple-black 93A at maturity.

*Hardiness.*—Zone 5.

*Fragrance.*—Foliage and wood are aromatic (mint-like) when crushed.

*Growth.*—Each branch or shoot that emerges in the spring gives rise to 20–30 auxiliary shoots prior to inflorescence initiation. New shoots grow quickly.

*Plant habit.*—Bushy, compact, low-growing and mounded.

*Propagation.*—Semi-ripe cuttings.

*Root system.*—Fibrous roots are fine and well-branched.

*Size.*—2 year old plants: 76 cm in height, 91 cm in width.

*Time to initiate new roots.*—6–10 days at 68° C. under mist.

*Time to develop roots.*—6–8 weeks, with 2 weeks under mist.

*Wood.*—Mature wood is semi-rough and streaked light tan 164D and grey-green 197B.

*Softwood is grey-brown 199B.*—Typically 10–16 secondary branches off a leader.

*Winter dormancy.*—Twiggy, branching habit.

Flower description:

*Flower type.*—Compound, dense, dichasial cymes.

*Bud.*—Up to 6 mm in diameter, color 94A.

*Calyx.*—Deeply 5-lobed, campanulate, 4 mm in length but enlarges as fruit develops.

*Corolla.*—Petals are fused, deeply 5-lobed, spreading, short-tubed 1–2 mm in length, 4 petal lobes are 7 mm in length; one lobe is longer, concave and flares up to 13 mm in length with fringed edges. Width 9–10 mm, Petal color 94B (opening), 94C (mature).

Reproductive organs:

*Stamens.*—4, exserted, pollen, very fine, moderate in quantity color 3C Anther 0.75 mm in length, 0.5 mm in width prior to filament color, Filament color 90C.

*Pistil.*—Stigma 2-cleft, Style exserted, Style color 90C. Ovary superior, 2 mm in length and 1 mm in width at bloom, color 193A.

Foliage description:

*Arrangement.*—Opposite and decussate, insertion is petiolate.

*Type.*—Deciduous, simple.

*Shape.*—Ovate-lanceolate, no lobes.

*Surface.*—Glabrous with satin appearance on upper surface, canescent on lower surface.

*Apex.*—Acute.

*Base.*—Attenuate.

*Margins.*—Entire to dentate.

*Venation.*—Upper surface: mid-vein recessed, secondary veins are recessed and pinnate. Lower surface: mid-vein and secondary veins prominent.

*Color.*—Upper surface 137A, lower surface 191A and midrib vein 146C, petiole is 146B on upper surface and 146C on lower surface.

*Size.*—Length: 3.5–6 cm, Width: 1–2 cm, Petiole length: 0.5–1 cm. Internode length: 2–3 cm.

COMPARISON WITH OTHER CULTIVARS

In Table I, the new invention, 'First Choice', is compared to the cultivar 'Dark Knight' (unpatented) because it is known for the dark color of its blooms. The foliage color of 'Dark Knight' (unpatented) is more similar to most other cultivars in the trade than 'First Choice'. In Table II, the mature plant size is compared with two other cultivars.

TABLE I

| | 'First Choice' | 'Dark Knight' (unpatented) |
|---|---|---|
| Foliage: | | |
| Shape | ovate-lanceolate | lanceolate |
| Length | 3.5–6 cm | 3.4–5.5 cm |
| Width | 1–2 cm | .5–1.5 cm |
| Petiole | .5–1 cm | .5–1 cm |
| Internode | 2–3 cm | 2–3.5 cm |
| Color: Adaxial | 137A | 144A |
| Abaxial | 191A | 147C |
| Surface: Adaxial | Satin Sheen | Dull |
| Angle to Stem | 45° | 60° |
| Flowers: | | |
| Number per compound cyme group | 15–30 | 9–19 |
| Bloom color: | 94B (Opening) 94C (Mature) | 94C (Opening) 94D (Mature) |
| Bud color: | 95A | 96D |
| Flower Size: Length | 13 mm | 11 mm |
| Width | 10 mm | 9 mm |

TABLE II

| Plant Size: | 'First Choice' | 'Long. Blue' (unpatented) | 'Kew Blue' (unpatented) |
|---|---|---|---|
| Height | 76 cm | 91 cm | 91 cm |
| Spread | 91 cm | 122 cm | 91 cm |

I claim:

1. The new and distinct cultivar of Caryopteris plant named 'First Choice' substantiated by the descriptions and illustrations herein.

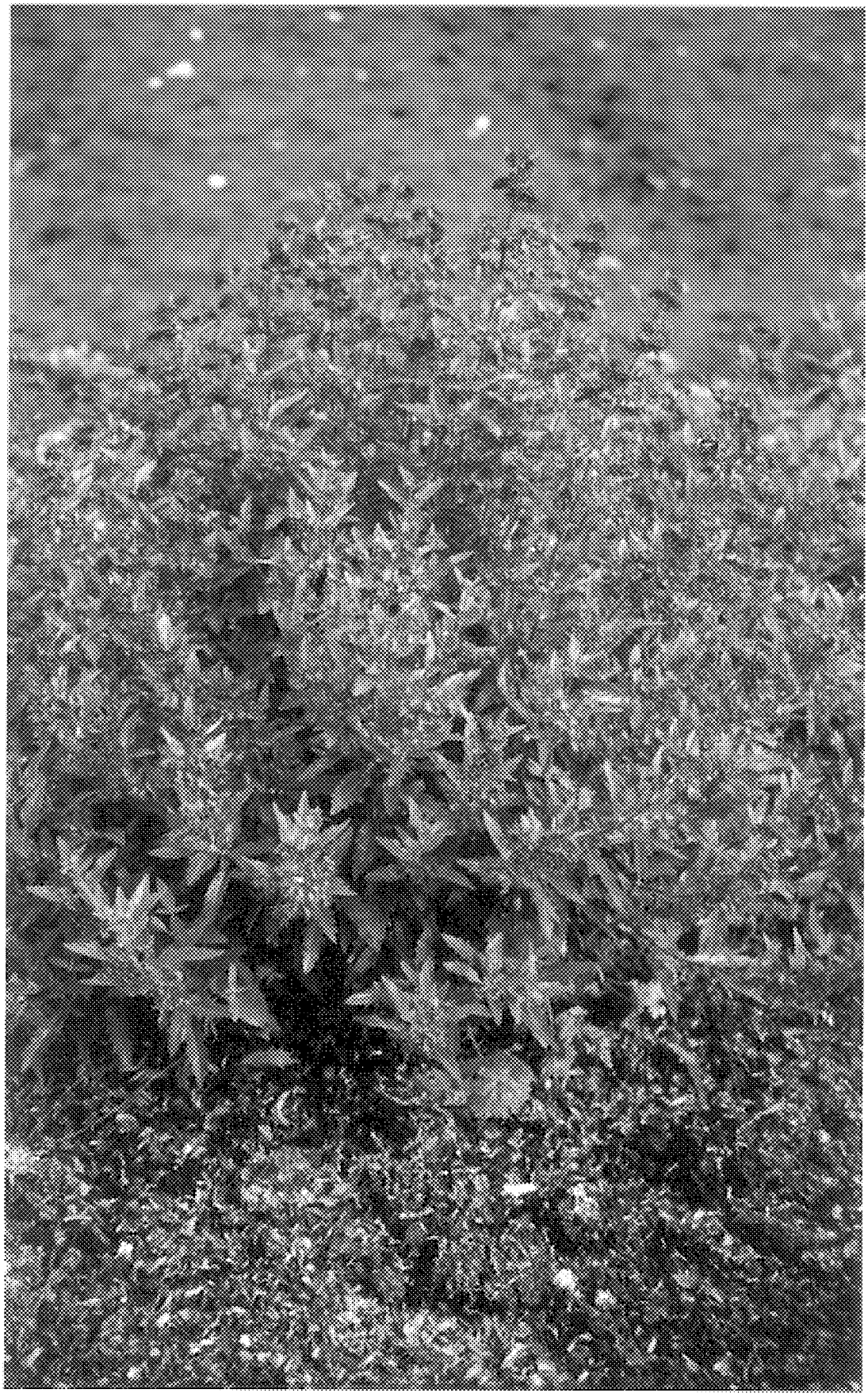

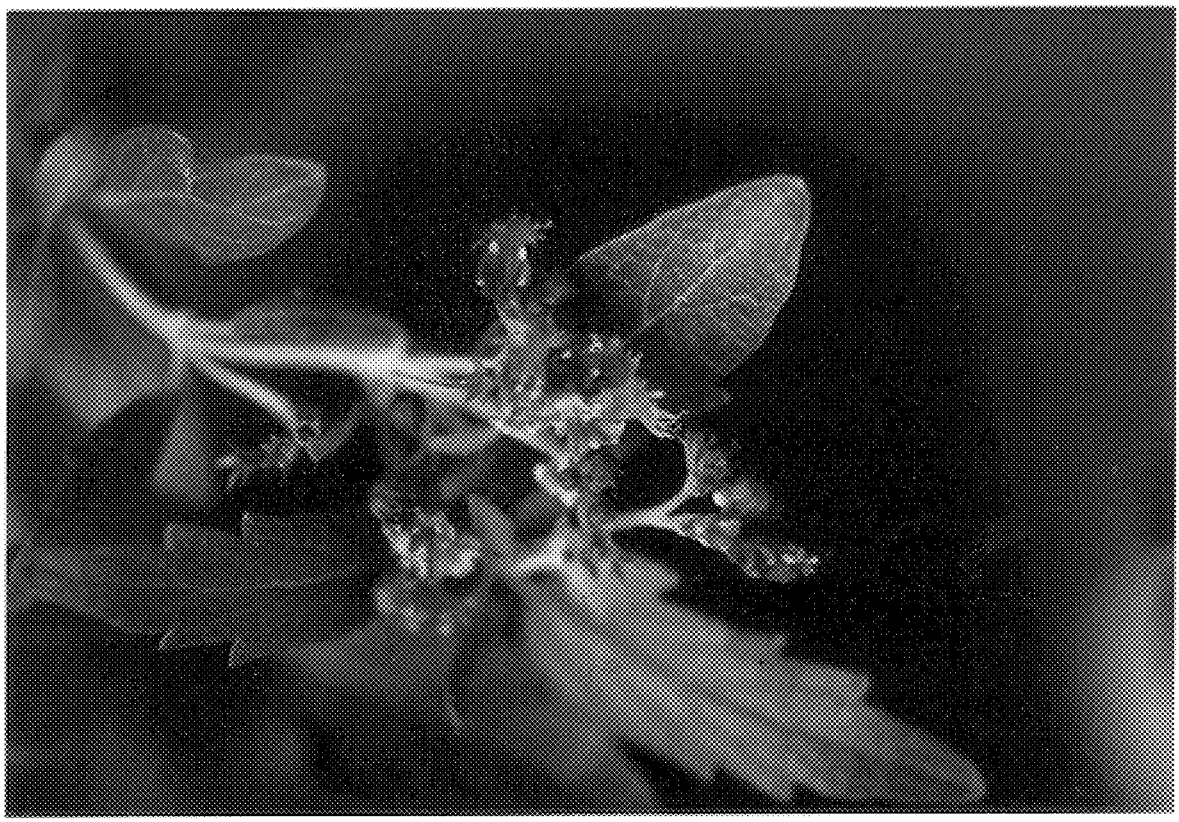
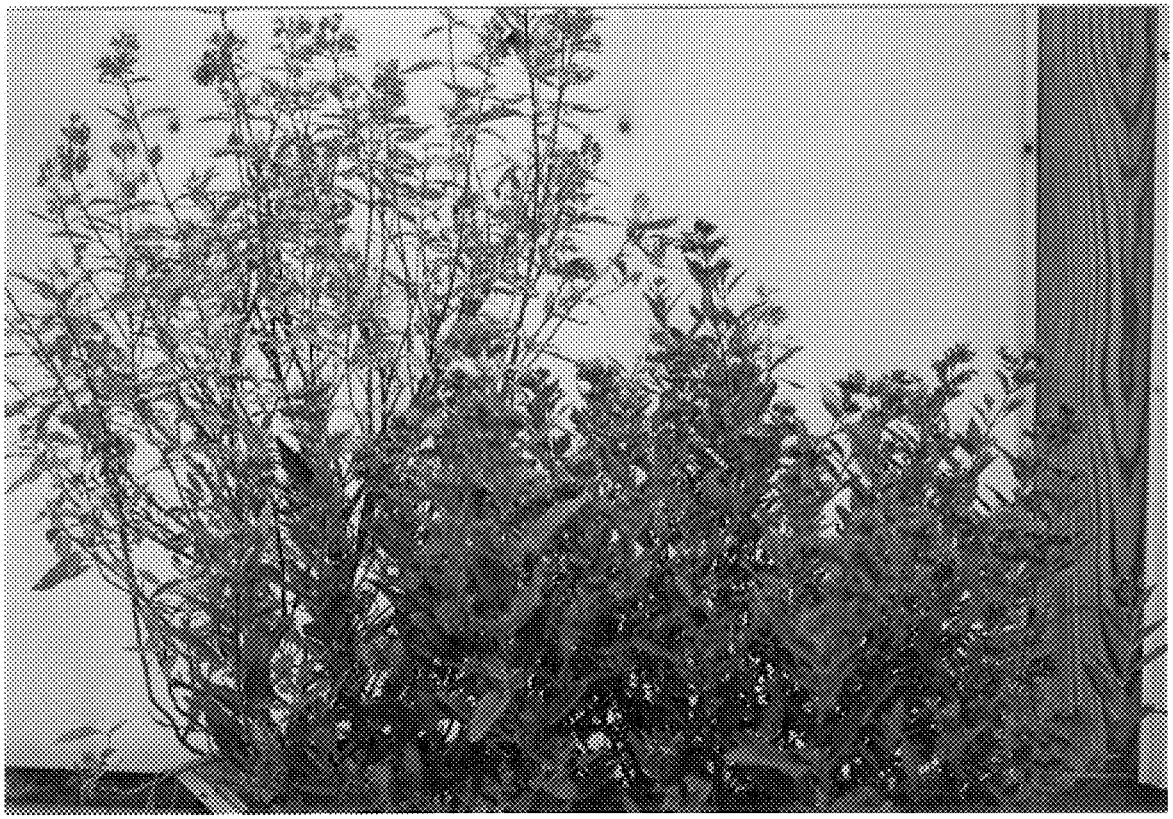

* * * * *